United States Patent
Pozzer et al.

(10) Patent No.: US 11,059,770 B2
(45) Date of Patent: Jul. 13, 2021

(54) PROCESS FOR PURIFICATION OF VINYL ACETATE FOR USE IN POLYMERIZATION IN THE PRESENCE OF ETHYLENE

(71) Applicant: Braskem S.A., Camacari (BR)

(72) Inventors: Dihogenes Adriano Pozzer, Sao Paulo/SP (BR); Olavo Martins Junior, Sao Paulo/SP (BR); Alessandra Coelho Silva Lucas, Sao Paulo/SP (BR); Iuri Freytag, Sao Paulo/SP (BR)

(73) Assignee: Braskem, S.A., Camaçari (BR)

( * ) Notice: Subject to any disclaimer, the term of this patent is extended or adjusted under 35 U.S.C. 154(b) by 0 days.

(21) Appl. No.: 16/471,201

(22) PCT Filed: Dec. 19, 2017

(86) PCT No.: PCT/IB2017/001679
§ 371 (c)(1),
(2) Date: Jun. 19, 2019

(87) PCT Pub. No.: WO2018/115961
PCT Pub. Date: Jun. 28, 2018

(65) Prior Publication Data
US 2020/0115315 A1 Apr. 16, 2020

Related U.S. Application Data

(60) Provisional application No. 62/436,765, filed on Dec. 20, 2016.

(51) Int. Cl.
*C07C 67/56* (2006.01)
*C08F 6/00* (2006.01)
(Continued)

(52) U.S. Cl.
CPC .......... *C07C 67/56* (2013.01); *B01J 20/3408* (2013.01); *B01J 20/3458* (2013.01); *C08F 6/00* (2013.01); *C08F 218/08* (2013.01); *C07C 69/15* (2013.01)

(58) Field of Classification Search
CPC . C07C 67/56; C07C 69/15; C08F 6/00; C08F 218/08; B01J 20/3408; B01J 20/3458
See application file for complete search history.

(56) References Cited

U.S. PATENT DOCUMENTS 3,080,433 A * 3/1963 Hengstebeck ............ C07C 7/13
585/824
3,509,115 A * 4/1970 French .................. C08F 218/08
528/481

(Continued)

OTHER PUBLICATIONS

De Lucas et al., "Removal of Acetic Acid by Adsorption from an Ethylene Recycle Stream in the Ethylene—Vinyl Acetate Copolymerization Process," Separation Science and Technology, 1999; 34(3): 525-543.

(Continued)

*Primary Examiner* — Yate' K Cutliff
(74) *Attorney, Agent, or Firm* — Duane Morris LLP (57) ABSTRACT

Process for purification of unreacted vinyl acetate monomers comprising the steps of preliminarily loading an adsorbent agent bed with a mixture comprising an inert gas and fresh vinyl acetate; and feeding said adsorbent agent bed with unreacted vinyl acetate monomers to remove acetic acid.

12 Claims, 5 Drawing Sheets

(51) Int. Cl.
*B01J 20/34* (2006.01)
*C08F 218/08* (2006.01)
*C07C 69/15* (2006.01)

(56) References Cited

U.S. PATENT DOCUMENTS

| | | | |
|---|---|---|---|
| 4,091,200 A | 5/1978 | Vandegaer | |
| 4,379,940 A * | 4/1983 | Dickerson | C07C 67/56 560/248 |
| 2005/0215733 A1 * | 9/2005 | Tsai | C08F 6/003 526/68 |
| 2011/0275852 A1 | 11/2011 | Kotsianis et al. | |
| 2015/0315119 A1 * | 11/2015 | Neumann | C07C 67/52 526/64 |

OTHER PUBLICATIONS

De Lucas et al., "Removal of Acetic Acid by Absorption from Stream Recycle Ethylene in the Ethylene and Vinyl Acetate Copolymers Process," Separation Science and Technology, 1992; 27(10): 1197-1210.

International Search Report, PCT/IB2017/001679, dated Jul. 11, 2018.

Anthony M. Wachinski; Fundamental Principles and Concepts of Ion Exchange from Environmental Ion Exchange Principles and Design, Published online on: Sep. 29, 2016, 51 pages.

Stephen Brunauer et al.; On a Theory of the van der Waals Adsorption of Gases, Jul. 1940, 10 pages.

E.F. Cuddihy et al.; Applications of Ethylene Vinyl Acetate as an Encapsulation Material for Terrestrial Photovoltaic Modules, Apr. 15, 1983, 80 pages.

International Union of Pure and Applied Chemistry—Compendium of Chemical Terminology Gold Book, Mar. 23, 2012, 1670 pages.

Michael D. Kempe, et al.; Acetic Acid Production and Glass Transition Concerns with Ethylene-Vinyl Acetate Used in Photovoltaic Devices, Jul. 19, 2006, 15 pages.

Zhenjun Li, et al.; The Adsorption and Reaction of Vinyl Acetate on Au—Pd (100) Alloy Surfaces, http://dx.doi.org/10.1016/j.susc.2012.03.011, pp. 1113-1119.

Ronald Ferreira Do Nascimento, et al.; Adsorção: Aspectos Teóricos e Aplicações Ambientais, 2014, 258 pages.

Mogon Patel, et al.; Thermal Stability of Poly(ethylene-co-vinyl acetate) Based Materials, http://dx.doi.org/10.1016/i.polymertesting.2013.03.014, pp. 785-793.

G.A. Razuvaev et al.; Thermal Degradation of Ethylene-Vinyl Acetate Copolymer, Polymer Letters Edition, 1973, vol. II, pp. 521-523.

Thu Tran et al.; Investigation of the Mechanism for Acetic Acid Corrosion of Mild Steel, Paper No. 2487, 2013 NACE International Corrosion Conference & Expo, 12 pages.

Odivan Zanella; Produção de Carvão Ativado a Partir do Engaço da Uva e Estudo da Regeneração Eletroquímica do Mesmo em um Reator Desenvolvido em Escala Laboratorial, 2015, 116 pages.

\* cited by examiner

PROCESS FOR PURIFICATION OF VINYL ACETATE FOR USE IN POLYMERIZATION IN THE PRESENCE OF ETHYLENE

FIELD OF THE INVENTION

The present invention refers to a purification process of the vinyl acetate monomer for use in the polymerization process to produce ethylene vinyl acetate copolymers (EVA).

BACKGROUND OF THE INVENTION

The ethylene vinyl acetate copolymer is a polymer obtained by the copolymerization of ethylene and vinyl acetate, commonly containing 8 wt % to 40 wt % bonded of vinyl acetate, based on total weight of ethylene vinyl acetate copolymer.

The copolymerization of ethylene and vinyl acetate occurs by free radical reaction wherein an initiator, preferably an organic peroxide, is subjected at thermal activation forming free radicals that disrupt the ethylene double bonds as shown in Equation 1.

$$ROOR^1 \rightarrow RO\cdot + R'O\cdot \rightarrow R'O\cdot + CH_2=CH_2 \rightarrow RO-CH_2-CH_2\cdot. \quad (Eq.\ 1)$$

Subsequently, the propagation chain step is initiated wherein a radical of the end of the chain approximates to another ethylene or vinyl acetate molecule, due to high pressure within the polymerization reactor, to disrupt the double bond and incorporate a monomer, as shown in Equation 2, or a comonomer, as shown in Equation 3. Among the macroscopic properties that may be mentioned there are mechanical properties, barrier properties, thermal and electrical conductivity and others.

$$(\ldots)CH_2-CH_2\cdot + CH_2=CH_2 \rightarrow (\ldots)CH_2-CH_2-CH_2-CH_2\cdot. \quad (Eq.\ 2)$$

$$(\ldots)CH_2-CH_2\cdot + CH_2=CH-OC(O)CH_3 \rightarrow (\ldots)CH_2-CH_2-CH_2-CH_2-C-C(OCOCH_3)H. \quad (Eq.\ 3)$$

Vinyl acetate is preferably incorporated, due to the polar characteristic that stabilizes the intermediate transition states, forming during monomer adding from the end of the chain, reducing the activation energy of its incorporation as described by Peacock (Handbook of Polyethylene: Structure, Properties and Applications, 1st ed, 2000).

During the propagation chain step occurs either a transference chain wherein the free radical from the end of the chain subtracts a hydrogen from the center chain. Polymeric chains interrupt its propagation after a termination reaction, that may be an intermolecular transference chain or a chain transfer agent, referred as telogen or CTA-, as showed in Equation 4.

$$(\ldots)CH_2-CH_2\cdot + CTA-H \rightarrow (\ldots)CH_2-CH_3 + CTA\cdot. \quad (Eq.\ 4)$$

Another form to interrupt the polymeric chain propagation is by a reaction of free radical from the end of the chain with another radical that may be from another polymeric chain, as showed in the Equations 5 and 6.

$$(\ldots)CH_2-CH_2\cdot + \cdot CH_2-CH_2(\ldots) \rightarrow (\ldots)CH_2-CH_2-CH_2-CH_2(\ldots) \quad (Eq.\ 5)$$

$$(\ldots)CH_2-CH_2\cdot + \cdot CH_2-CH_2(\ldots) \rightarrow (\ldots)CH_2-CH_3 + CH=CH_2-CH_2(\ldots) \quad (Eq.\ 6)$$

Furthermore, polymeric chain propagation can be interrupted by an initiation moiety, as showed in Equation 7.

$$(\ldots)CH_2-CH_2\cdot + RO\cdot \rightarrow (\ldots)CH_2-CH_2-OR \quad (Eq.\ 7)$$

Vinyl acetate, on polymerization reaction to produce ethylene vinyl acetate copolymers, acts as a monomer and transfer agent chain, reducing chain length.

Figure 1:
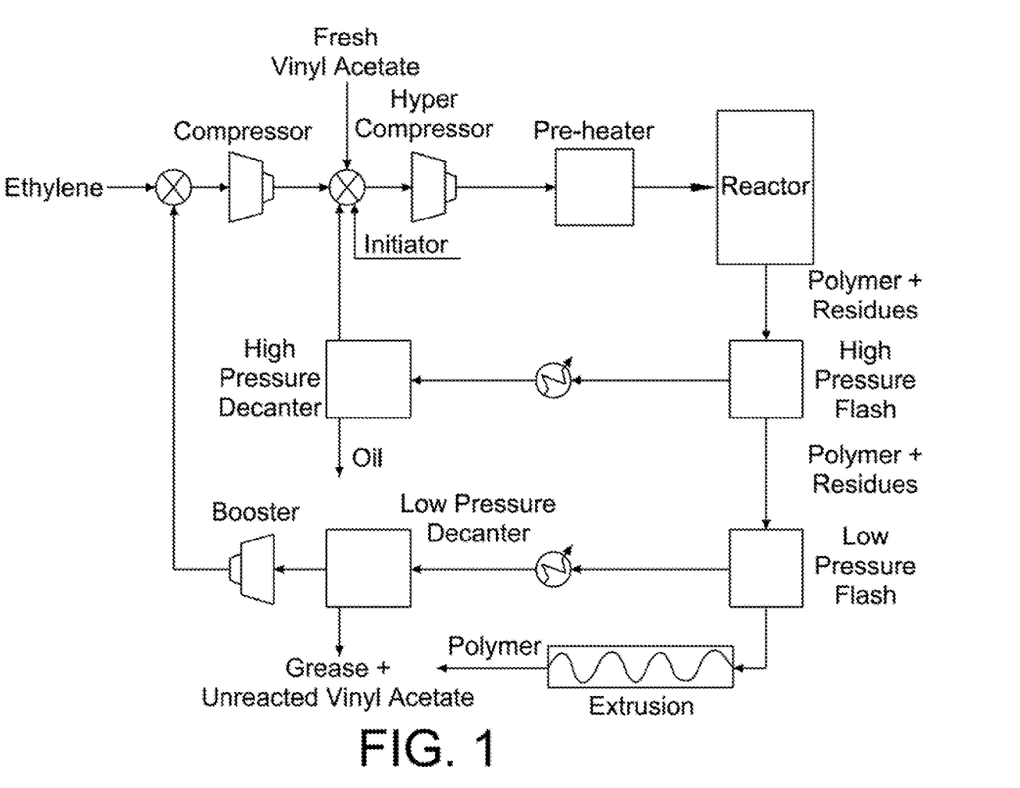
FIG. 1 depicts a schematic flow diagram for an ethylene vinyl acetate (EVA) production process.

FIG. 1 depicts a generic process to produce ethylene vinyl acetate copolymers comprising: (a) providing a first reciprocating compressor to pressurize ethylene monomer; (b) introducing ethylene monomer from step (a) on a second reciprocating compressor, referred to as hyper-compressor to pressurize ethylene monomer; (c) contacting ethylene monomer from step (b), initiator and vinyl acetate comonomer; (d) pre-heating the mixture from step (c); (e) contacting in a reactor train the mixture from step (d) to produce ethylene vinyl acetate copolymer; (f) separating the polymer-residues phase forming in the step (e) passing through a high pressure flash vessel, separating the polymer-enriched phase from light residues phase; (g) separating the unreacted ethylene monomer from the light residues phase passing through a high pressure decanter vessel; (h) rejecting the oil from step (g); (i) separating the polymer-enriched from step (f) from the heavy residues phase passing through a low pressure flash vessel; (j) separating the unreacted ethylene monomer from the heavy residues phase passing through low pressure decanter vessel; (k) rejecting the grease and unreacted vinyl acetate; (l) pressurizing the ethylene from step (j) and introducing in the first reciprocating compressor downstream on step (a); (m) submitting the polymer from step (l) at extrusion process.

Figure 2:
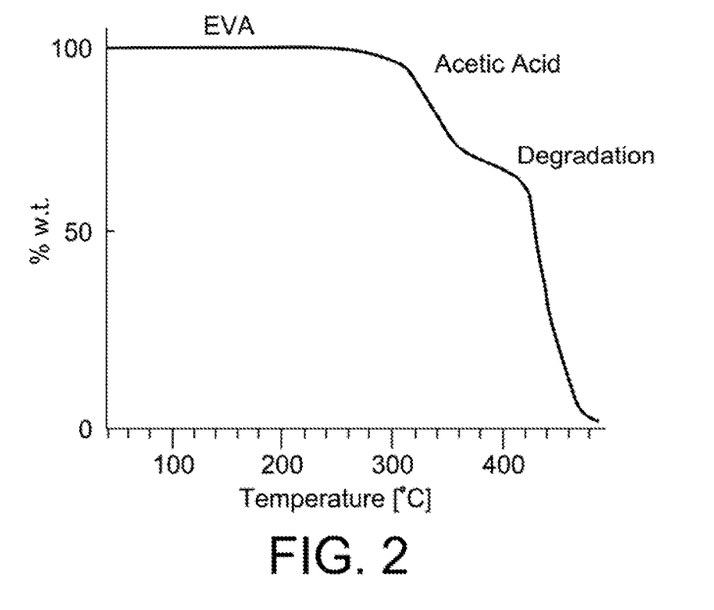
FIG. 2 depicts a thermogram of EVA with 28% wt. of vinyl acetate with heating rate of 10° C./min.

Although there are no references in the literature concerning the mechanisms responsible for acetic acid generation on an ethylene vinyl acetate polymerization process, it is possible due to certain causes. As described by Allen et al. (Polymerization Degradation and Stability, vol 68, n.3, 2000, 363-371), ethylene vinyl acetate subjected at temperatures near 280° C. may generate acetic acid by thermal degradation as showed in FIG. 2. Another mechanism may be the hydrolysis of acetate groups from ethylene vinyl acetate chains, as shown in Equation 8.

$$(\ldots)CH_2-C(OCOCH_3)H-CH_2(\ldots) + H_2O \rightarrow (\ldots)CH_2-C(OH)H-CH_2(\ldots) + CH_3COOH \quad (Eq.\ 8)$$

Vinyl acetate monomer may be subjected at hydrolysis to form acetic acid, previously to its incorporation into the polymer.

Manufacturers of vinyl acetate monomer have specifications of 50 ppm by weight acetic acid (max) and 400 ppm by weight water (max).

Posteriorly to ethylene vinyl acetate polymerization, unreacted vinyl acetate may contain 100 times more acetic acid than the fresh vinyl acetate. Supposing reuse of unreacted vinyl acetate on the polymerization reactor, unreacted vinyl acetate may contain 1000 times more acetic acid than fresh vinyl acetate.

Due to this high acetic acid concentration, the reuse of the unreacted vinyl acetate in the polymerization is limited. This high acetic acid concentration may cause corrosion in pipelines and equipment in the polymerization plants. To preserve the pipelines and equipment, most of producers reject the unreacted vinyl acetate or reuse the unreacted vinyl acetate moiety, reducing the polymerization temperature to minimize the acetic acid generation. Consequently, the ethylene vinyl acetate copolymer production is a high-cost process due to low vinyl acetate conversion and the necessity of equipment and pipelines to have constant maintenance due to corrosion caused by acetic acid.

Usually the vinyl acetate is not treated on the polymerization process to produce ethylene vinyl acetate copolymers. The vinyl acetate purification step occurs on the supplier process. For example, U.S. Pat. No. 3,905,875 describes a process for purification of crude liquid vinyl acetate by distillation.

U.S. Pat. No. 4,878,959 describes a process for purifying vinyl acetate using a dehydrated anion exchange resin to remove acetic acid and a dissecant to remove water.

On the other hand, U.S. Pat. No. 3,318,548 describes a process for purifying the vinyl acetate combining distillation and activated carbon.

The process of the present invention provides a low-cost purification treatment which will remove the acetic acid and water from vinyl acetate monomer without the disadvantages from the previous processes.

DETAILED DESCRIPTION OF THE INVENTION

In one embodiment of the present invention, the process for purification of unreacted vinyl acetate monomer comprises the steps of preliminarily loading an adsorbent agent bed with a mixture comprising an inert gas and fresh vinyl acetate; and feeding said adsorbent agent bed with unreacted vinyl acetate monomer to remove acetic acid.

The "unreacted vinyl acetate monomer" of the present invention is preferably vinyl acetate monomer recovered from the EVA polymerization process.

The inert gas used in the present invention is preferably nitrogen or saturated hydrocarbon. The saturated hydrocarbon may be selected among methane, ethane, propane, butane and combinations thereof.

The preliminary load is preferably performed with a mixture comprising an inert gas and fresh vinyl acetate at low concentration, wherein the acetic acid adsorption occurs at controlled conditions. The preliminary contact of adsorbent agent with the mixture of vinyl acetate and inert gas is necessary to control the heating generated in the reaction due to vinyl acetate adsorption. After this controlled adsorption, the unreacted vinyl acetate is fed into the adsorbent agent bed to remove acetic acid.

Optionally, water is removed from the fresh vinyl acetate monomer before the polymerization process step and, optionally, water is removed from the unreacted vinyl acetate monomer before the acetic acid removal step.

In a preferred embodiment, the process for purification of unreacted vinyl acetate monomers comprises the steps of
1) Drying a fresh vinyl acetate monomer stream in a molecular sieve bed;

2) Subjecting the fresh vinyl acetate to a polymerization process in the presence of ethylene to produce EVA polymer;

3) Recovering the unreacted vinyl acetate monomers from the polymerization process;

4) Drying said unreacted vinyl acetate monomer in a molecular sieve bed;

5) Preliminarily loading an adsorbent agent bed with a mixture comprising an inert gas and fresh vinyl acetate at low concentration;

6) Feeding the adsorbent agent bed with the dried unreacted vinyl acetate monomers to remove the acetic acid.

The obtained purified vinyl acetate is suitable to be recycled to the polymerization process to produce ethylene vinyl acetate copolymers (EVA).

Eventually, the molecular sieve may become fully loaded with water and the adsorbent agent bed may become fully loaded with acetic acid. In this case, a regeneration process of said beds may be necessary.

Preferably, in the dehydration steps (1) and (4), the vinyl acetate monomers are dried by feeding them through the beds of a molecular sieve at room temperature and positive pressure. Also, said molecular sieve beds may be previously dehydrated with inert gas at high temperature.

In step (5), the preliminary loading occurs with a mixture of fresh vinyl acetate and an inert gas at room temperature.

In step (6), the acetic acid present in dried unreacted vinyl acetate is removed, preferably, by feeding the dried unreacted vinyl acetate through the adsorbent agent bed, at room temperature and positive pressure, therefore obtaining a purified vinyl acetate that may be recycled to the polymerization process.

In a most preferred embodiment, the process for purification of unreacted vinyl acetate monomers comprises the steps of
1) Subjecting a molecular sieve bed to a dehydration treatment at a temperature range of 170 to 270 deg C., preferably between 250 and 270 deg C., at a pressure range of 0 and 760 mmHga, preferably between 0 and 76 mmHga, for a period of time varying between 2 and 24 hours, preferably from 2 to 8 hours, by contacting said bed with an inert gas;

2) Passing a fresh vinyl acetate (previously stored in a vessel at pressure range of 0 and 2280 mmHga, preferably between 760 and 1520 mmHga) through the molecular sieve bed at room temperature at the same pressure range of fresh vinyl acetate storage vessel. The fresh vinyl acetate stream may be recycled to a storage vessel until fresh vinyl acetate is completely dried. The fresh vinyl acetate may pass through the molecular sieve bed and recycled to a storage vessel for a period varying between 2 and 24 hours, preferably from 2 to 8 hours. Alternatively, the fresh vinyl acetate may pass through a dehydrated molecular sieve bed at room temperature, at a pressure range of 22.800 mmHga and 228.000 mmHga, preferably from 22.800 mmHga and 38.000 mmHga;

3) Feeding a polymerization reactor with the fresh and dried vinyl acetate and performing the polymerization process in the presence of ethylene to obtain the ethylene vinyl acetate copolymer;

4) Separating the unreacted vinyl acetate from the polymer and unreacted ethylene;

5) Passing the unreacted vinyl acetate through a dehydrated molecular sieve bed at room temperature at pressure range of 0 do 2280 mmHga, preferably between 760 and 1520 mmHga to remove water from unreacted vinyl acetate monomer;

6) Subjecting an adsorbent agent bed to a dehydration treatment at a temperature range of 170 to 270 deg. C., preferably between 250 deg. C. and 270 deg. C., at pressure range of 760 and 3040 mmHga, preferably between 1140 and 1900 mmHga, for a period of time varying between 2 and 24 hours, preferably between 2 and 8 hours, by contacting said bed with an inert gas;

7) Subjecting the adsorbent agent bed of step 6 to a preliminary load by contacting the adsorbent agent with a mixture of fresh vinyl acetate and an inert gas, at temperature below 100 deg. C. or below 50 deg. C. or at room temperature, at pressure range of 760 to 3040 mmHga, preferably between 760 and 1900 mmHga, at a ratio of 0.1 to 50% by weight, preferably between 0.1 and 10% by weight of fresh vinyl based on the weight of the mixture, for a period of time varying between 30 and 1440 minutes, preferably between 30 and 600 minutes;

8) Passing the dried unreacted vinyl acetate obtained in step 5 through the dehydrated preloaded adsorbent agent of step 7 at room temperature, at pressure range of 760 and 228 mmHga, preferably between 760 and 1520 mmHga for remove water and acetic acid from unreacted vinyl acetate monomer.

After the molecular sieve beds and adsorbent agent beds are saturated, it may be necessary to subject said beds to a regeneration step. Preferably, the regeneration process comprises the following steps:

a. Feeding the molecular sieve and or adsorbent agent beds with an inert gas at room temperature, at pressure range of 760 and 3040 mmHga, preferably between 1140 and 1900 mmHga for a period of time varying between 2 and 24 hours, preferably between 2 and 6 hours;

b. Feeding said beds with an inert gas at temperature range of 30 to 110 deg. C., for a period of time varying between 2 and 24 hours, preferably between 2 and 12 hours;

c. Subjecting said beds to a dehydration treatment with inert gas, at a temperature range from 170 to 270 deg. C., preferably between 250 and 270 deg. C., at pressure range of 760 and 3040 mmHga, preferably between 1140 and 1900 mmHga, for a period of time varying between 2 and 24 hours, preferably from 2 to 8 hours, by passing an inert gas through said beds.

According to the present invention, the molecular sieve dryer may be a crystalline aluminosilicate with a sodalite unit type X, as shown in Equation 9 or a sodalite unit type Y, as shown in Equation 10,

| | | |
|---|---|---|
| $NA_{12}(AlO_2)_{12}(SiO_2)_{12}$ | Type X | (Eq. 9) |
| $NA_6(AlO_2)_6(SiO_2)_{18}$ | Type Y | (Eq. 10) | forming molecular sieve type A, X or Y with porous diameter between 3 Å and 13 Å.

Further, according to the present invention, the molecular sieve dryer used in the dehydration of fresh vinyl acetate monomer and unreacted vinyl acetate monomer may be alumina in 7×14 Tyler mesh with nominal ball size between ⅛ and ¼ inch of diameter.

The adsorbent agent of the present invention used to remove acetic acid may be selected from alumina in 7×14 Tyler mesh with nominal ball size between ⅛ and ¼ inch of diameter or a molecular sieve type X or Y with porous diameter between 4 Å and 13 Å.

The purified vinyl acetate obtained by the process of the present invention may contain an amount of acetic acid below 3000 ppm wt, or below 1000 ppm wt or even below 200 ppm wt.

The purified vinyl acetate obtained by the process of the present invention may contain an amount of water below 3000 ppm wt, or below 1000 ppm wt or even below 200 ppm wt.

EXAMPLES

Example 1

76.1 g of activate carbon was added on 200 mL of vinyl acetate monomer, at room temperature in a stirred Schlenk flask under nitrogen atmosphere. The mixture of active carbon and vinyl acetate was stirred during 2 hours.

Table 1 shows the acetic acid concentration reduction in an unreacted vinyl acetate sample according the treatment method of example 1.

TABLE 1

| | Before Treatment | After Treatment |
|---|---|---|
| Acetic Acid (ppm w.t.) | >40.000 | 29.614 |

The vinyl acetate solubilized partially the activate carbon which makes the activate carbon unviable on industrial application.

Example 2

50 g of alumina (Basf Selexorb®CD) was added in 200 mL of vinyl acetate monomer, at room temperature in a stirred Schlenk flask under nitrogen atmosphere. The mixture of alumina and vinyl acetate was stirred during 2 hours.

Table 2 shows the acetic acid concentration according to the method of Example 2 and the result of Example 1 for comparative analysis.

TABLE 2

| Adsorbent Agent | Example 2 Alumina | Comparative Example 1 Activate Carbon |
|---|---|---|
| Acetic Acid concentration Before Treatment (ppm w.t.) | >40.000 | >40.000 |
| Acetic Acid concentration After Treatment (ppm w.t.) | 2.580 | 29.614 |

As shown in Table 2, the alumina was more efficient than activate carbon to remove the acetic acid from an unreacted vinyl acetate sample. On the other hand, the vinyl acetate did not solubilize alumina turning its industrial application viable.

Example 3

500 g alumina (Basf Selexsorb CD) was added in a stainless steel column. The alumina was subjected at preliminary load feeding through a bed of a mixture of nitrogen containing 10% by weight of vinyl acetate monomer during 4 hours. After preload was fed vinyl acetate monomer containing 22078 ppm wt. of acetic acid. During testing, 17 liters of vinyl acetate monomer was treated.

Figure 3:
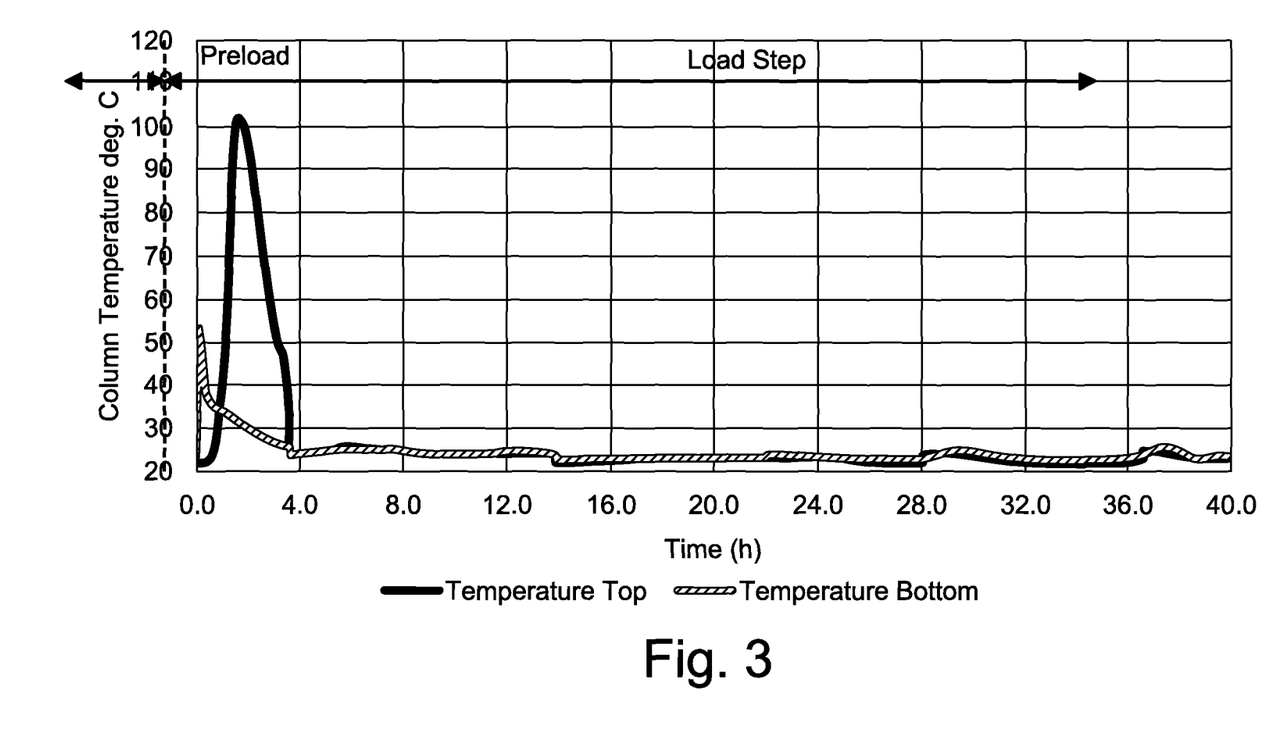
FIG. 3 is a graph (corresponding to Example 3) which shows the temperature from the top and bottom of the column during preload and vinyl acetate treatment steps.

FIG. 3 shows the temperature from the top and bottom of the column during preload and vinyl acetate treatment steps.

As shown in FIG. 3, the temperature of the bed during the preload step was 102 deg. C. and after the temperature remained at 30 deg. C.

Figure 4:
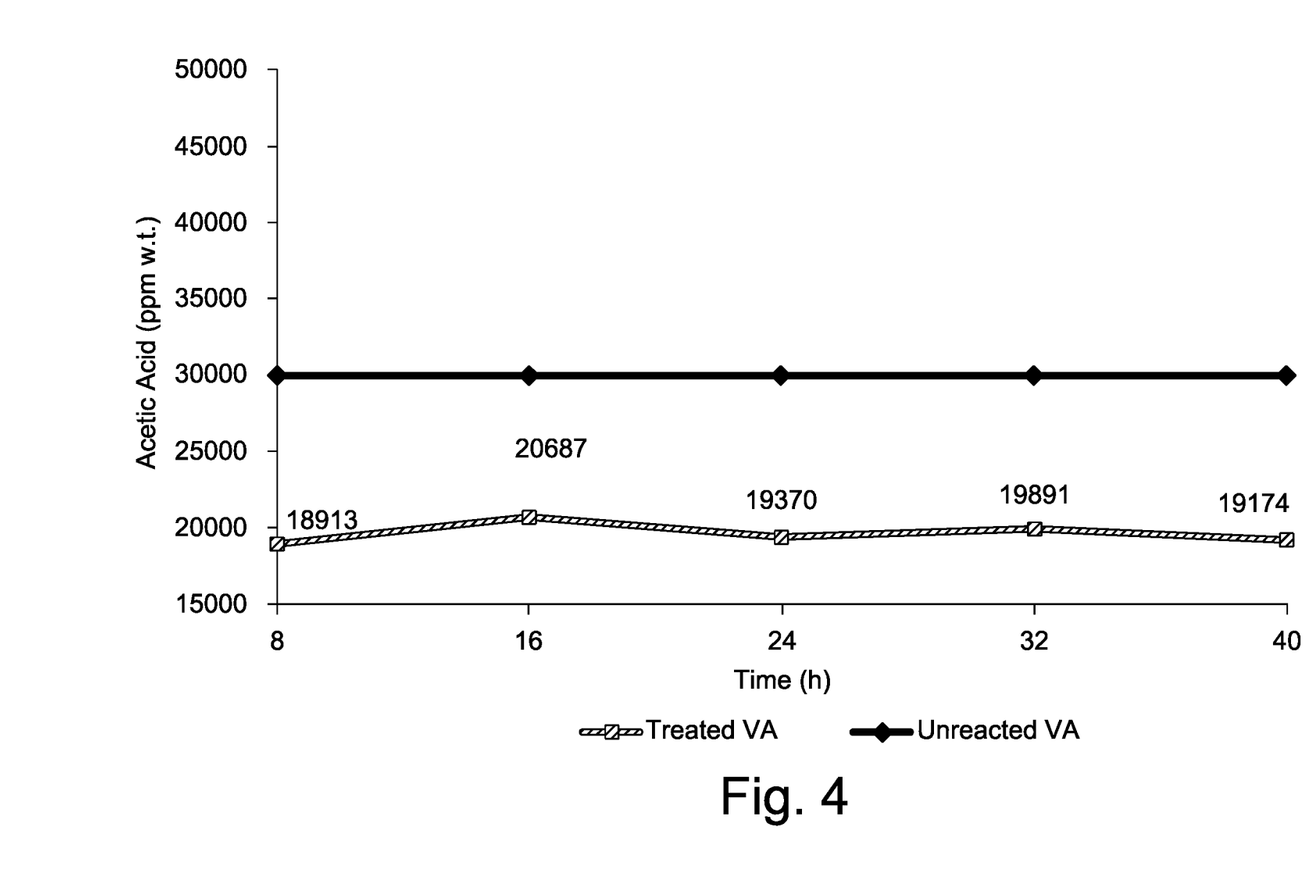
FIG. 4 is a graph (corresponding to Example 3) which shows acetic acid concentration during vinyl acetate monomer treatment.

FIG. 4 shows acetic acid concentration during vinyl acetate monomer treatment.

As shown in FIG. 4, the adsorption ratio was 10.6%, near to 1 g alumina adsorbing 0.106 g of acetic acid.

Example 4

500 g of alumina (Basf Selexsorb CD) was dried in an oven with nitrogen at 270 deg. C. for 4 hours, and then added in a stainless steel column. The alumina was subjected at preliminary load feeding through a bed of a mixture of nitrogen containing until 13% by weight of vinyl acetate monomer for 10 hours. After preload, vinyl acetate monomer containing until 48.770 ppm wt. of acetic acid was fed. During testing, 20.4 liters of vinyl acetate monomer was treated.

Figure 5:
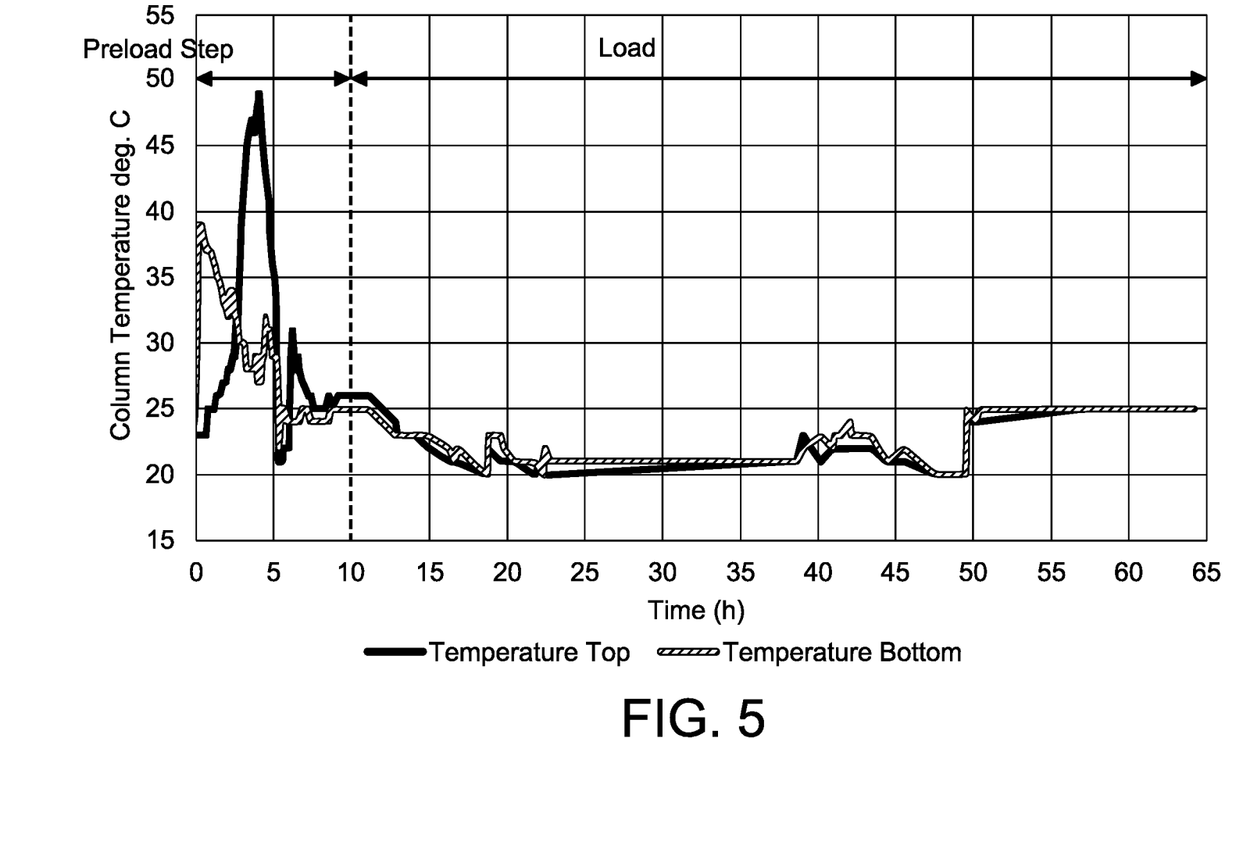
FIG. 5 is a graph (corresponding to Example 4) which shows the temperature from the top and bottom of the column during the preload and vinyl acetate treatment step.

FIG. 5 shows the temperature from the top and bottom of the column during the preload and vinyl acetate treatment step.

As shown in FIG. 5, the temperature of the bed during the preload step was 49 deg. C. and after the temperature remained at 28 deg. C.

Figure 6:
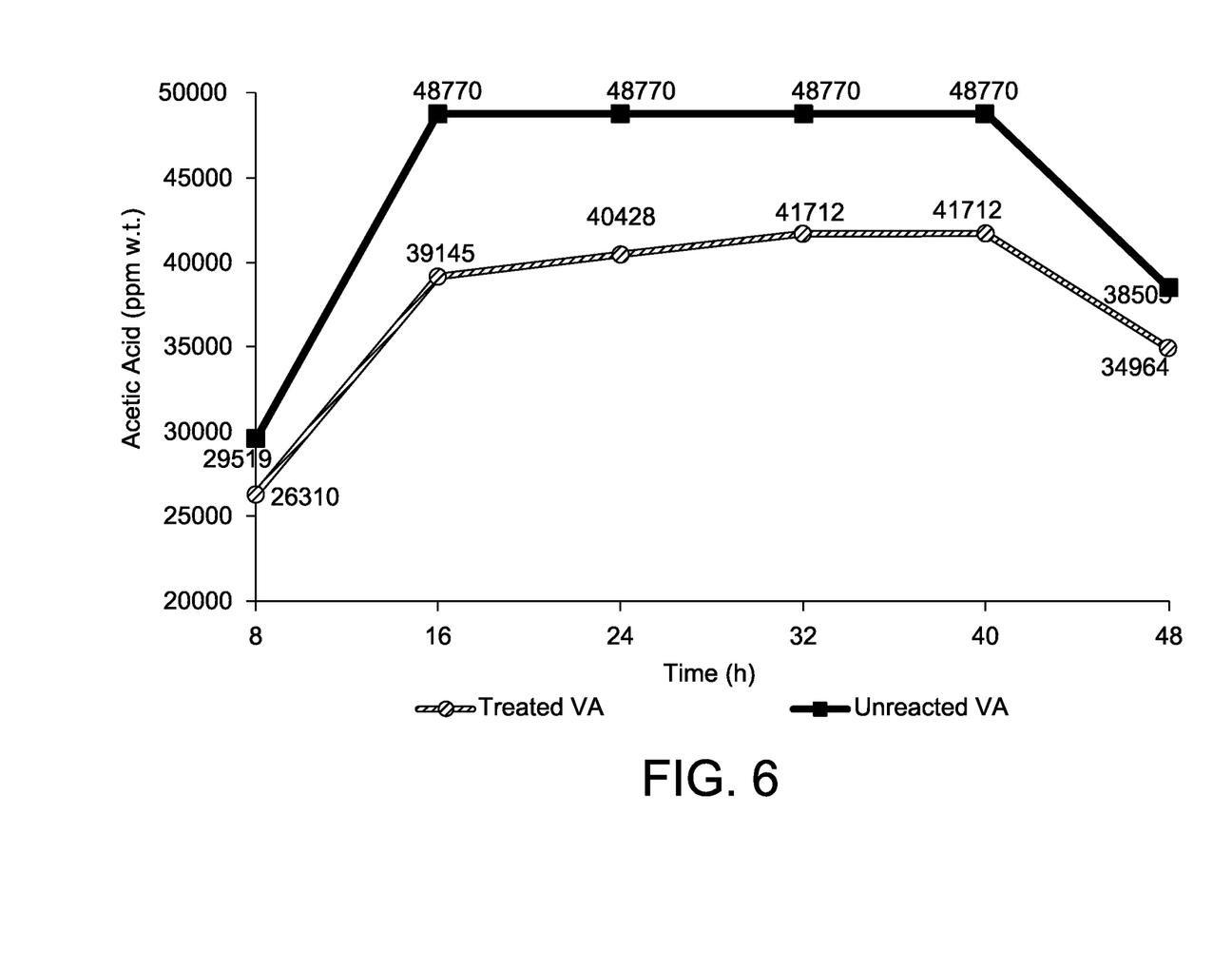
FIG. 6 is a graph (corresponding to Example 4) which shows acetic acid concentration during vinyl acetate monomer treatment.

FIG. 6 shows acetic acid concentration during vinyl acetate monomer treatment.

As shown in FIG. 6, the adsorption ratio was 26.4%; this means that 1 g of alumina adsorbs 0.264 g of acetic acid.

What is claimed is:

1. A process for purification of unreacted vinyl acetate monomers comprising:
    i) drying a fresh vinyl acetate monomer stream in a molecular sieve bed;
    ii) subjecting the fresh vinyl acetate to a polymerization process in the presence of ethylene to produce an ethylene vinyl acetate (EVA) polymer;
    iii) recovering unreacted vinyl acetate monomers from the polymerization process;
    iv) drying the unreacted vinyl acetate monomers in the molecular sieve bed;
    v) preliminarily loading an adsorbent agent bed with a mixture comprising an inert gas and the fresh vinyl acetate at low concentration; and
    vi) feeding the adsorbent agent bed with dried unreacted vinyl acetate monomers to remove the acetic acid,
wherein the unreacted vinyl acetate monomer is a vinyl acetate monomer recovered from the EVA polymerization process, and the inert gas is a nitrogen or saturated hydrocarbon selected from the group consisting of methane, ethane, propane, butane and combinations thereof.

2. The process according to claim 1, wherein in the dehydration steps i) and iv) the vinyl acetate monomers are dried by feeding through the molecular sieve bed at room temperature and positive pressure.

3. The process according to claim 1, further comprising subjecting the molecular sieve bed to a dehydration treatment at a temperature range of 170 to 270° C., and at a pressure range of 0 and 760 mmHga for a period between 2 and 24 hours, by contacting said bed with an inert gas.

4. The process according to claim 1, further comprising subjecting the molecular sieve bed to a dehydration treatment at a temperature range between 250 and 270° C., and at a pressure range between 0 and 76 mmHga, for from 2 to 8 hours, by contacting said bed with inert gas.

5. The process according to claim 1, wherein the fresh vinyl acetate is previously stored in a vessel at pressure range of 0 and 2280 mmHga and passed through the molecular sieve bed at room temperature and at the same pressure range of the fresh vinyl acetate storage vessel.

6. The process according to claim 1, wherein in step ii) a polymerization reactor is fed with fresh and dried vinyl acetate and a polymerization process is performed in the presence of ethylene to obtain ethylene vinyl acetate copolymer.

7. The process according to claim 6, wherein the unreacted vinyl acetate is separated from the copolymer and the unreacted ethylene.

8. The process according to claim 6, wherein the step iv) comprises passing the unreacted vinyl acetate through the molecular sieve bed at room temperature and at a pressure range of 0 to 2280 mmHga.

9. The process according to claim 1, wherein the step v) further comprises subjecting the adsorbent agent bed to a dehydration treatment at a temperature range of 170 to 270° C., and at a pressure range of 760 and 3040 mmHga, for a period between 2 and 24 hours, by contacting said bed with the inert gas.

10. The process according to claim 9, wherein in step v) the adsorbent agent bed is subjected to a dehydration treatment at a temperature range between 250° C. and 270° C., and at a pressure range between 1140 and 1900 mmHga, for a period between 2 and 8 hours, by contacting said bed with the inert gas.

11. The process according to claim 9, wherein in step v) the adsorbent agent bed further comprises a preliminary load by contacting the adsorbent agent with a mixture of fresh vinyl acetate and inert gas at a temperature below 100° C., at pressure range of 760 and 3040 mmHga, and at a ratio of 0.1% to 50% by weight of fresh vinyl acetate based on the weight of mixture for between 30 and 1440 minutes.

12. The process according to claim 11, further comprising the preliminary load at a temperature below 100° C., at a pressure range from 760 to 1900 mmHga, and at a ratio of 0.1 and 10% by weight of fresh vinyl acetate based on the weight of the mixture, for between 30 and 600 minutes.

* * * * *